(12) United States Patent
Haas et al.

(10) Patent No.: US 6,693,222 B2
(45) Date of Patent: Feb. 17, 2004

(54) PROCESS FOR SPLITTING WATER-SOLUBLE ETHERS

(75) Inventors: Thomas Haas, Frankfurt (DE); Christian Ronge, Aargau (CH); Torsten Hahn, Mahwah, NJ (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/136,083

(22) Filed: Apr. 29, 2002

(65) Prior Publication Data

US 2003/0187308 A1 Oct. 2, 2003

Related U.S. Application Data

(60) Provisional application No. 60/356,308, filed on Feb. 12, 2002.

(51) Int. Cl.$^7$ .......................... C07C 43/11; C07C 31/20
(52) U.S. Cl. ...................... 568/866; 568/619; 568/680
(58) Field of Search ................................ 568/619, 680, 568/866

(56) References Cited

U.S. PATENT DOCUMENTS

| | | | |
|---|---|---|---|
| 5,364,987 A | * | 11/1994 | Haas et al. |
| 6,218,580 B1 | * | 4/2001 | Morawietz et al. |
| 6,235,948 B1 | | 5/2001 | Sunkara et al. |
| 6,331,264 B1 | | 12/2001 | Kurian et al. |

FOREIGN PATENT DOCUMENTS

| CH | 502 971 | 3/1971 |
|---|---|---|
| EP | 0 577 972 A1 | 1/1994 |
| EP | 0 915 075 A1 | 5/1999 |

OTHER PUBLICATIONS

C.A. Rojahn; Polyether of Trimethyleneglycol; Oct. 29, 1921 Berichte der deutschen chemischen Gesellschaft (54):3118–3121 (1921) (translation).
EPO Search Report dated Apr. 24, 2001.

* cited by examiner

*Primary Examiner*—Samuel Barts
*Assistant Examiner*—Sikarl A. Witherspoon
(74) *Attorney, Agent, or Firm*—Mark D. Kuller

(57) ABSTRACT

A process for production of 1,3-propanediol including the steps: (a) hydrating acrolein in the presence of an acid hydration catalyst; (b) catalytically hydrogenating the reaction mixture of step (a), which reaction mixture comprises 3-hydroxypropionaldehyde and is freed of unreacted acrolein; (c) refining the reaction mixture of step (b) containing water, 1,3-propanediol and the by-products boiling higher than 1,3-propanediol; and, (d) treating 4-oxa-1,7-heptanediol to form 1,3-propanediol by (1) removing a boiler sump comprising 4-oxa-1,7-heptanediol from the refining step (c), (2) treating the boiler sump in an aqueous solution in the presence of an acid catalyst at about 200 to about 300° C. to form a solution comprising 1,3-propanediol, (3) neutralizing the solution obtained is step (2), and returning the neutralized solution from step (3) to the refining step (c). In addition, a process for splitting oligomeric water-soluble ether comprising: (a) treating an aqueous solution comprising oligomeric water-soluble ether in the presence of homogeneous acid catalyst at a temperature of from about 200 to about 300° C. to form the monomer of the oligomeric water-soluble ether; and (b) neutralizing the solution obtained in step (a),

29 Claims, No Drawings

PROCESS FOR SPLITTING WATER-SOLUBLE ETHERS

FIELD OF THE INVENTION

The invention concerns a process for the splitting of water-soluble ethers. The invention also concerns a process for the production of 1,3-propanediol (PDO).

BACKGROUND OF THE INVENTION

Generally ethers can be split in the gas phase, such as the splitting of n-butylalkyl ethers or n-butylaryl ethers into butene and alcohols or phenols, or the splitting of esters, vinyl ethers and alkenes with beta-positioned chlorine in the pipe reactor of Vycor glass into unsaturated chlorine compounds such as vinyl chloride. Another example is gas phase pyrolysis with benzylphenyl ether in a glass container in the presence of tetraline.

Ether splitting in the liquid phase is also possible. For instance, the pyrolysis of dibutyl ether in a gold reactor into n-butane, butyraldehyde and also 1-butanol.

For the splitting of the ethers both subcritical and supercritical solvents can also be used. For instance, thermolysis of benzylphenyl ether in subcritical and supercritical water and supercritical methanol, results in, among others, phenol and toluene.

Ethers such as 1-phenoxynaphthalene and 9-phenoxyphenanthrene are capable of being split by so-called aquathermolysis in a pipe of V4A steel only in the presence of water into 1-napthene and 9-hydroxyphenathrene and phenol respectively.

U.S. Pat. No. 6,218,580 (counterpart to EP 0 915 075), which is incorporated herein by reference, teaches that the acid-catalyzed intermolecular etherification of mono- or polyhydric alcohols and acid-catalyzed ether cleavage in the presence of water can be improved if etherification or ether cleavage is carried out in the presence of an acid catalyst with a hydrogenation catalyst under a hydrogen atmosphere. Comparison Example 2 describes cleavage of dipentaerythritol with propionic acid in water wherein the reaction mixture is heated to 280° C.

As is known from U.S. Pat. No. 5,364,987 (counterpart to EP 0 577 972), which is incorporated herein by reference, processes for the production of 1,3-propanediol from acrolein are generally based on two reaction steps. The first step, step (a), comprises hydration of acrolein in the presence of an acid hydration catalyst. The second step, step (b), comprises catalytic hydrogenation of the reaction mixture containing 3-hydroxypropionaldehyde from step (a), which reaction mixture has been freed of unreacted acrolein. (Preferably, acrolein levels can be reduced to about 200 ppm or less.) The processes also comprises step (c), distillative refining of the reaction mixture. Pure 1,3-propanediol (which can contain as much as 99.9 weight % or more 1,3-propanediol) is obtained by distillative refining of the reaction mixture in step (c), i.e. evaporation of the water, the distillation of the residual water, intermediate boiler distillation (removing low boiling compounds) and distillation-purification.

The disadvantage of the known process for the production of 1,3-propanediol is the fact that due to various secondary reactions, especially during the hydration step, the total yield of 1,3-propanediol is reduced. During the refining of the reaction mixture from the catalytic hydrogenation, the high boiler fraction (boiling point above that of 1,3-propanediol) contains as primary products 4-oxa-1,7-heptanediol (DiPDO) (also known as 3,3'-oxybis-1-propanol or bis(3-hydroxypropyl)ether) and 4-hydroxy-3-hydroxymethyl tetrahydropyran (HMT, in the form of two isomers H-HMT1 and H-HMT2).

U.S. Pat. No. 5,364,987 teaches a process comprising (1) distilling the aqueous 1,3-propanediol mixture which contains by-products having boiling points higher than 1,3-propanediol; (2) separating DiPDO from the by-products having boiling points higher than 1,3-propanediol; and treating the DiPDO in aqueous solution at from 100–300° C. with an solid acid catalyst in order to cleave DiPDO to form 1,3-propanediol; and returning the resulting reaction mixture from which the solid acid catalyst has been removed to the distilling step. U.S. Pat. No. 5,364,987 teaches that separation of DiPDO is necessary, whereas it is desired that such a separation not be used, i.e., that the high boiler sump accumulating in the process can be utilized directly.

Other processes for the producing of 1,3-propanediol can also result in the production of DiPDO and conversion of DiPDO to 1,3-propanediol would also be beneficial to these processes.

One object of this invention is to provide a simple and effective method for splitting or cleaving oligomeric water-soluble ethers.

Another objective of the present invention is to provide a method for increasing the yield of 1,3-propanediol in the process for the production of 1,3-propanediol from acrolein in a simple way.

Other objectives will become evident from the following description of the invention.

SUMMARY OF THE INVENTION

The invention is directed to a process for production of 1,3-propanediol including the steps: (a) hydrating acrolein in the presence of an acid hydration catalyst; (b) catalytically hydrogenating the reaction mixture of step (a), which reaction mixture comprises 3-hydroxypropionaldehyde and is freed of unreacted acrolein; (c) refining the reaction mixture of step (b) containing water, 1,3-propanediol and the by-products boiling higher than 1,3-propanediol; and (d) treating 4-oxa-1,7-heptanediol to form 1,3-propanediol by (1) removing a boiler sump comprising 4-oxa-1,7-heptanediol from the refining step (c), (2) treating the boiler sump in an aqueous solution in the presence of an acid catalyst at about 200 to about 300° C. to form a solution comprising 1,3-propanediol, (3) neutralizing the solution obtained is step (2), and returning the neutralized solution from step (3) to the refining step (c).

The invention can be used to treat any such sump. According to a preferred process of making 1,3-propanediol, the sump preferably contains at least about 50 weight %, preferably at least about 55 weight %, 4-oxa-1,7-heptanediol. It preferably contains up to about 70 weight %, more preferably up to about 65 weight %, 4-oxa-1,7-heptanediol.

Preferably water is added to the boiler sump to form the aqueous solution. Preferably the water is added so that the ratio of organic compounds in the sump:water (organic:water ratio) is at least about 0.5:1, preferably at least about 1:1. Preferably, the organic:water ratio is up to about 1:20, more preferably up to about 1:8.

In one preferred embodiment, the boiler sump further comprises 4-hydroxy-3-hydroxymethyl tetrahydropyrane.

The invention is also directed to a process for splitting oligomeric water-soluble ether comprising: (a) treating an aqueous solution comprising oligomeric water-soluble ether in the presence of homogeneous acid catalyst at a temperature of from about 200 to about 300° C. to form the monomer of the oligomeric water-soluble ether; and (b) neutralizing the solution obtained in step (a). Preferably, the oligomeric water-soluble ether is selected from the group consisting of $C_4$–$C_7$ ethers and mixtures thereof, more preferably the group consisting of 4-oxa-1,7-heptanediol, diethyleneglycol dimethyl ether, diglycol, dipropyleneglycol, dipropyleneglycol methyl ether, and propyleneglycol methyl ether. Preferably, the aqueous solution further comprises organic compounds having boiling points higher than the oligomeric water-soluble ether. In the most preferred embodiment, the oligomeric water-soluble ether is 4-oxa-1,7-heptanediol and the monomer is 1,3-propanediol. In that embodiment, the organic compounds having boiling points higher than the oligomeric water-soluble ether comprise 4-hydroxy-3-hydroxymethyl tetrahydropyran.

The acid catalyst is preferably a mineral acid, which is preferably selected from the group consisting of $H_2SO_4$, $H_3PO_4$ or $HNO_3$, and mixtures thereof.

Alternatively, the acid catalyst is preferably an organic acid, which is preferably selected from the group consisting of propionic acid, trifluoracetic acid or pyridine hydrochloride, and mixtures thereof.

The acid catalyst is used in an amount of at least 0.05 weight %, more preferably at least about 0.5 weight %, based on the oligomeric ether being split, e.g., DiPDO. It is preferably used in an amount of up to 5 weight %, more preferably up to 2 weight %, based on the oligomeric ether being split.

Preferably the process is a continuous process.

The processes preferably have a selectivity of at least 50% and a yield of at least 50%.

The processes are preferably carried out in the absence of a hydrogenation catalyst.

DETAILED DESCRIPTION OF THE INVENTION

The subject of the invention is a process for splitting or cleaving water-soluble ethers. The process comprises treating an aqueous solution of the ethers in the presence of acids at 200–300° C. and the solution obtained neutralized.

By "oligomeric water-soluble ether" reference is to ethers with at least two monomeric units and at least one ether bridge. As the ether, one can use $C_4$–$C_7$ ethers and mixtures thereof. In particular the process of the invention can be applied to the following ethers: 4-oxa-1,7-heptanediol (DiPDO); diethyleneglycol dimethyl ether (Diglyme); diglycol; dipropyleneglycol (DiPg); dipropyleneglycol methyl ether (Di PG Me); and propyleneglycol methyl ether (PG PE).

Ether splitting operations are preferably conducted in aqueous solution in the presence of homogeneous acid catalyst (that is, catalysts that are soluble in the aqueous solution in the amount used, and which are not solid catalysts), such as mineral acids and organic acids. Preferred mineral acids are $H_2SO_4$, $H_3PO_4$ or $HNO_3$. Organic acids such as propionic acid (PrA), trifluoracetic acid ($F_3C$—COOH) or pyridine hydrochloride can also be used. Other useful homogeneous catalysts can be selected from the group consisting of Lewis Acids, Bronsted Acids, super acids, and mixtures thereof. Examples include fluorosulfonic acid, phosphorous acid, p-toluenesulfonic acid, benzenesulfonic acid, phosphotungstic acid, and trifluoromethanesulfonic acid. The most preferred catalyst is sulfuric acid.

The process should be carried out in a pipe or vessel suitable for handling the reaction, i.e., that is capable of handling hot acids. Preferred is a tantalum pipe or vessel. Steel, such as Zircolloy or Hastelloy, or glass-lined pipes or vessels can also be used.

Preferably the acid or acid catalyst is used in an amount of at least 0.05 weight %, more preferably at least about 0.5 weight %, based on the oligomeric ether being split, e.g., DiPDO. It is preferably used in an amount of up to 5 weight %, more preferably up to 2 weight %, based on the oligomeric ether being split.

The invention is also directed to a process for production of 1,3-propanediol. Hydrating acrolein in the presence of an acid hydration catalyst, and catalytically hydrogenating the reaction mixture (which comprises 3-hydroxypropionaldehyde and is substantially free of unreacted acrolein), can be carried out using known methods.

Preferably the reaction mixture comprising 3-hydroxypropionaldehyde is freed of unreacted acrolein by a separation step that occurs between steps (a) and (b). The separation can be carried out by distillation or other means of removing acrolein. A small portion of acrolein can remain after this step, but for the purpose of this invention the 3-hydroxypropionaldehyde is considered freed of unreacted acrolein. (Preferably, acrolein levels are reduced to about 200 ppm or less.)

The reaction mixture of step (b) containing water, 1,3-propanediol and the by-products boiling higher than 1,3-propanediol is refined, preferably by distillation. (The reaction mixture also contains some intermediate compounds, i.e., compound with boiling points in-between the boiling points of water and 1,3-propanediol, which are distilled off with the water.)

The 4-oxa-1,7-heptanediol that is formed during the reaction is treated to form 1,3-propanediol (PDO). Boiler sump (also called "PDO sump solution") comprising 4-oxa-1,7-heptanediol is removed from the refining step (c). Then, the sump is treated in an aqueous solution in the presence of acid at about 200 to about 300° C. to form a solution comprising 1,3-propanediol. The invention can be used to treat any such sump. According to a preferred process of making 1,3-propanediol, the sump preferably contains at least about 50 weight %, preferably at least about 55 weight %,4-oxa-1,7-heptanediol. It preferably contains up to about 70 weight %, more preferably up to about 65 weight %, 4-oxa-1,7-heptanediol. Such a sump preferably contains hydroxy-3-hydroxymethyl tetrahydropyran (HMT) in an amount of at least about 20 weight %, more preferably at least about 25 weight %, and preferably up to about 40 weight %, more preferably up to about 35 weight %. High boiling compounds are typically present in an amount of up to 10 weight %, more preferably up to 5 weight %, probably as sludge. To form the aqueous solution water is added to the sump. Preferably the water is added so that the weight ratio of organic compounds in the sump:water (organic:water ratio) is at least about 0.5:1, preferably at least about 1:1. Preferably, the organic:water ratio is up to about 1:20, more preferably up to about 1:8. The resulting solution is neutralized. Preferably it is neutralized using calcium hydroxide, but other bases can be used (e.g., calcium carbonate, magnesium hydroxide, etc.) The base should be used in an amount suitable to remove the acid, e.g., about stoichiometric amounts. Then, the neutralized solution is returned to the refining step.

The process can be carried out using continuous or batch techniques, with continuous processes being preferred.

U.S. Pat. No. 5,364,987 (counterpart to EP 0 577 972) teaches that separation of DiPDO from the sump is necessary. An advantage of the process of the invention is the fact that the high boiler sump accumulating in the process can be utilized directly. No byproducts are formed which cannot be removed, as has been asserted.

Another advantage is that the solid catalysts described in U.S. Pat. No. 5,364,987 have a short service life. The acid used in the invention, such as mineral acid catalysts, can be removed by an ion exchanger. Ion exchangers can be regenerated. Alternatively, an insoluble salt (in the case of $H_2SO_4$) can be formed by the addition of $Ca(OH)_2$, which is then filtered off.

The neutralized solution can be distilled together with the crude 1,3-propanediol stream of the installation without problem in the available refining without modification, i.e., it can be returned for use in step (c). No quality loss occurs.

The processes are preferably carried out in the absence of a hydrogenation catalyst, for instance, as described in U.S. Pat. No. 6,218,580, which is incorporated by reference.

High yield is achieved through high selectivity and high conversion for the desired product (e.g., 1,3-propanediol). Selectivity is preferably at least 30%, more preferably at least 40%, even more preferably at least 50%, and most preferably at least 60%. Conversion is preferably at least 30%, more preferably at least 40%, even more preferably at least 50%, and most preferably at least 60%. Desirably they are as high as 70%, 80%, 90% or more.

EXAMPLES

This invention is demonstrated in the following examples, which are not intended to be limiting. Therein, all parts, percentages, etc., are by weight, unless otherwise indicated.

Experiments in DiPDO splitting (splitting of 4-oxa-1,7-heptanediol) were conducted continuously. The apparatus consisted of a receiving vessel for the aqueous DiPDO solution mixed with organic acid or with mineral acid, a HPLC (high performance liquid chromatography) pump for conveying, a GC (gas chromatography) oven in which the reaction pipe was installed. For the tests with propionic acid, a pipe of V4A steel (750×0.3 cm diameter) was used. For the experiments with sulfuric acid, a pipe of tantalum (58×0.3 cm diameter) was used. After the reaction, the reaction solution was cooled to room temperature by water cooling. The apparatus was held at a pressure of ca. 100 bar. The product solution was analyzed at certain time intervals by GC (area % by flame ionization detection).

Example 1

Splitting of Pure DiPDO With Propionic Acid

Pure DiPDO was split with propionic acid in a pipe reactor of V4A steel. Test conditions are presented in Table 1 and the analytic results in GC area percent in Table 2.

TABLE 1

Test Conditions.

| Test No. | Wt. % ratio DiPDO | $H_2O$ | Pr | $T_R$ (° C.) | Holding Time (minutes) | Operating Time-Reactor (hours) | DiPDO Conversion (%) | PDO Selectivity (%) |
|---|---|---|---|---|---|---|---|---|
| 1 | 2.3 | 16.7 | 1 | 300 | 62 | 5 | 15.6 | 35.9 |
| 2 | 2.3 | 16.7 | 1 | 300 | 123 | 6 | 20.2 | 48.3 |
| 3 | 2.3 | 16.7 | 1 | 300 | 252 | 5 | 30.0 | 55.6 |

PDO = 1,3-propanediol
Pr = propionic acid
$T_R$ = Temperature of Reaction

TABLE 2

Analytic Results

| Test No. | EtOH[1] | Ac[2] | PrOH[3] | PDO | 2M13PED[4]/ PrS-mPDO[5] | DiPDO | PrS-mDiPDO[6] | Tri-PDO | PrS-diDiPDO[7] | Quadruple PDO ether |
|---|---|---|---|---|---|---|---|---|---|---|
| 1 | 0 | 0.45 | 0.07 | 5.57 | 0.71 | 83.75 | 7.89 | 0.24 | 0 | 0.41 |
| 2 | 0 | 1.32 | 0.14 | 9.53 | 1.19 | 77.89 | 7.39 | 0.51 | 0.12 | 0.70 |
| 3 | 0.08 | 1.26 | 0.24 | 16.49 | 2.02 | 69.23 | 6.54 | 1.15 | 0 | 1.01 |

[1]Ethanol
[2]Acrolein
[3]1-propanol
[4]2-methyl-1,3-pentanediol
[5]Propanediolmonopropionate
[6]Dipropanediolmonopropionate
[7]Dipropanedioldipropionate This example shows that DiPDO can be cleaved into 1,3-propanediol using propionic acid. With increasing holding time, the conversion and selectivity increased. To be sure, in this case also the by-products such as Ac, PrOH, PrS-mPDO, TriPDO and quadruple PDO ether also increase, while the PrS-mDiPDO formation regresses. Upon an increase in the reaction temperature to 320° C. and at the same holding time (123 minutes) the conversion rose from 20.2% to 32.3% and the selectivity rose from 48.3% to 54.6%. These values were also obtained with lower temperature and double holding time. The only disadvantage of propionic acid is the formation of esters with DiPDO, as well as PDO, which reduces the PDO yield. This can be controlled by selection of operating conditions.

Example 2

Splitting of Pure DiPDO With Sulfuric Acid

Pure DiPDO was split with sulfuric acid in a tantalum pipe. In these experiments, the weight percent ratio DiPDO:$H_2O$, $H_2SO4$ concentration (the latter always relative to the organics), temperature and holding time were varied.

Table 3 and 4 show the DIPDO conversions obtained and the PDO selectivity with the adjustments: DiPDO:$H_2O$ of 1:4 and 1:8 at temperatures of 250 and 280° C.

TABLE 3

| T = 250° C. $[H_2SO_4]$ = 0.5% | | | T = 280° C. $[H_2SO_4]$ = 0.5% | | |
|---|---|---|---|---|---|
| $t^8$ (h) | $U^9$ (%) | $S^{10}$ (%) | t (h) | U (%) | S (%) |
| Trial 1 DiPDO:$H_2O$ = 1:4 | | | Trial 2 DiPDO:$H_2O$ = 1:4 | | |
| 0.08 | 4.8 | 27.6 | 0.08 | 14.8 | 33.3 |
| 0.16 | 5.8 | 48.6 | 0.16 | 27.2 | 63.1 |
| 0.32 | 16.2 | 35.5 | 0.32 | 47.8 | 60.9 |
| 1 | 33.1 | 58.1 | 1 | 74.8 | 52.8 |
| 2 | 49.5 | 61.4 | | | |
| Trial 3 DiPDO:$H_2O$ = 1:8 | | | Trial 4 DiPDO:$H_2O$ = 1:8 | | |
| 0.08 | 2.1 | 34.3 | 0.08 | 4.8 | 80.2 |
| 0.16 | 1.9 | 98 | 0.16 | 14.4 | 74.5 |
| 0.32 | 6.0 | 70.6 | 0.32 | 29.6 | 73.9 |
| 1 | 20.2 | 65.5 | 1 | 64.1 | 68.5 |
| 2 | 35.9 | 68.6 | | | |

[8]Holding time
[9]Conversion
[10]Selectivity

TABLE 4

| T = 250° C. $[H_2SO_4]$ = 2.5% | | | T = 280° C. $[H_2SO_4]$ = 2.5% | | |
|---|---|---|---|---|---|
| t (h) | U (%) | S (%) | t (h) | U (%) | S (%) |
| Trial 5 DiPDO:$H_2O$ = 1:4 | | | Trial 6 DiPDO:$H_2O$ = 1:4 | | |
| 0.08 | 8.7 | 46.8 | 0.08 | 39.6 | 63.6 |
| 0.16 | 21.7 | 50.8 | 0.16 | 68.2 | 54.9 |
| 0.32 | 39.7 | 54.9 | 0.32 | 80.5 | 44.3 |
| 1 | 69.8 | 61.1 | | | |
| Trial 7 DiPDO:$H_2O$ = 1:8 | | | Trial 8 DiPDO:$H_2O$ = 1:8 | | |
| 0.08 | 4.8 | 50.5 | 0.08 | 25.2 | 64.3 |
| 0.16 | 11.0 | 65.4 | 0.16 | 51.7 | 69.7 |
| 0.32 | 23.7 | 65.6 | 0.32 | 74.2 | 59.9 |

Of the eight trials conducted, trials 2, 4, 5 and 8 crystallized out. Since it was found more advantageous to work with low $H_2SO4$ concentrations—considering the subsequent neutralization of the solution and accumulation of salts—the test parameters of trial 4 (with 1 hour holding time) were found to be optimal.

A high DiPDO concentration (wt. % ratio DiPDO:$H_2O$ of 1:1) led to high conversion (up to 87%), although the selectivity amounts to only 20%. Besides TriPDO, quadruple and quintuple PDO polyethers are formed intensively, which became noticeable visually as oily spots on the solution. If the DiPDO concentration, conversely, is relatively low (wt. % ratio DiPDO:$H_2O$ of 1:10), conversion (61%) and selectivity (73%) did indeed lie relatively high, but in turn the Ac content at ca. 4% was the highest of all of the experiments performed. At a very low $H_2SO_4$ concentration of only 0.05% only a little DiPDO was converted: 19% at 280° C.

Example 3

Splitting of DiPDO Contained in PDO Sump

DiPDO contained in the sump of PDO distillation product was split in a tantalum pipe. In addition to DiPDO, the PDO sump solution contained the two cis/trans isomers H-HMT1 and H-HMT2 at ca. 15 and 7%, respectively, in the organics. Since these compounds also contribute to PDO formation they were included in the conversion and selectivity calculations.

Various parameters were tested, with $H_2SO_4$ concentration always being maintained at 0.5% relative to the organics (Table 5 and 6).

TABLE 5

| Effect of Temperature (holding time 0.33 h) | | | |
|---|---|---|---|
| T (° C.) | Organic:$H_2O$ | DiPDO Conversion (%) | PDO Selectivity (%) |
| 150 | 1:8 | 0.6 | 23.7 |
| 250 | 1:8 | 4.5 | 22.6 |

At the short holding time of 0.33 hour, both conversion and selectivity were relatively low. Under these conditions, temperatures below 250° C. were unsuitable for DiPDO splitting.

With the test parameters listed in Table 6, the following conversions and selectivities were achieved.

TABLE 6

| Effect of DiPDO concentration at 250° C. | | | | | |
|---|---|---|---|---|---|
| T (° C.) | Organic:$H_2O$ | Holding Time (h) | Operating time reactor (h) | DiPDO conversion (%) | PDO selectivity (%) |
| 250 | 1:8 | 2 | 3 | 34.2 | 21.7 |
| | | | 4 | 22.5 | 36.9 |
| 250 | 1:4 | 2 | 3 | 54.7 | 24.8 |
| | | | 4 | 47.0 | 39.3 |
| 250 | 1:1 | 2 | 3 | 62.4 | 30.1 |
| | | | 4 | 61.7 | 30.0 |
| | | | 5 | 60.2 | 29.8 |

(h) = hours

The organic:$H_2O$ ratio of 1:1 in the educt solution results in high conversions precisely as in the case of pure DiPDO solution, but achieves relatively low selectivity. The more dilute solutions yield increasing conversions with increasing organic concentrations, the selectivities being almost the same (slight increase).

Results of the Optimal Test Parameters

Using the conditions T=280° C., organics:$H_2O$ 1:8, holding time 1 hour and $H_2SO_4$ concentration 0.5%, the invention obtained a conversion of 53% and a PDO selectivity of 44%.

Example 4

Refining

Neutralization of the Splitting Solution

The splitting solution was neutralized with aqueous $Ca(OH)_2$ solution and freed of precipitated $CaSO_4$ with subsequent filtration.

Distillation

A PDO reaction solution blended with splitting solution was refined by residual water distillation with subsequent intermediate boiler distillation and distillation-purification of the sump solutions obtained as in the case of the conventional PDO process. Distillation conditions are listed in Table 7.

TABLE 7

|  | Packing | T (° C.) | P (mbar) | Volume flow (ml/h) | Reflux ratio |
|---|---|---|---|---|---|
| Residual water distillation | Sulzer CY 1 m, 50 mm | 150 | 100 | 325–250 | 5:1 |
| Intermediate boiler distillation | Sulzer CY 1 m, 50 mm | 170 | 50 | 150 | 1:100 |
| Distillation-purification | Sulzer CY 1 m, 50 mm | 160 | 20 | 230 | 1:1 |

In the following, the product spectra obtained from the solutions obtained by distillation are compared with the solutions obtained by the conventional PDO process.

A pure product with 99.9% PDO was obtained. The purity of the PDO therefore remains uninfluenced despite the admixture of the splitting at the beginning of the distillation.

Example 5

Splitting of Various $C_4$–$C_7$ Ethers With Sulfuric Acid

Experiments were performed with the following water-soluble diethyleneglycol dimethyl ether (diglyme)

diglycol dipropylene glycol (DiPG)

dipropyleneglycol methyl ether (DiPGME)

propyleneglycol propyl ether (PGPE)

The reaction conditions were:

0.5% $H_2SO_4$ relative to the organic, 1 hour holding time, weight ratio ether:$H_2O$ of 1:8. The temperatures were varied from 150 to 280° C.

TABLE 8

Splitting solution (SL), Initial solutions (EL) and pure PDO solutions of distillations (Numerical format xx.xx = GC-FI % and xxxx = ppm)

| Substance | SL | EL RWD[11] new | EL RWD Old | EL ZSD[12] New | EL ZSD old | EL RD[13] new | EL RD old | Pure PDO solution new | Pure PDO solution old |
|---|---|---|---|---|---|---|---|---|---|
| MeOH[14] | 0.17 | 151 | 15 | 108 | 0 | 59 | 35 | 10 | 32 |
| EtOH | 0.13 | 117 | 222 | 0 | 0 | 0 | 0 | 0 | 0 |
| Ac | 0.99 | 436 | 337 | 63 | 18 | 20 | 154 | 26 | 146 |
| AllOH[15] | 0.35 | 280 | 0 | 0 | 0 | 0 | 0 | 0 | 0 |
| PrOH | 0.35 | 320 | 157 | 0 | 0 | 0 | 0 | 0 | 0 |
| HPA | 96 | 81 | 64 | 0 | 39 | 0 | 0 | 0 | 0 |
| Et-PDO[16] | 290 | 306 | 633 | 0 | 515 | 0 | 0 | 0 | 0 |
| PDO | 34.4 | 82.5 | 86.8 | 84.6 | 87.0 | 79.6 | 86.1 | 99.9 | 99.8 |
| 2M[13]PED | 153 | 588 | 161 | 338 | 125 | 55 | 76 | 80 | 106 |
| 3-HMT[17] | 3.59 | 0.51 | 0.11 | 0.42 | 0.10 | 131 | 117 | 58 | 62 |
| HED[18] | 0.27 | 0.34 | 0.53 | 0.29 | 0.53 | 11 | 397 | 49 | 350 |
| 2M[15]PED[19] | 294 | 0.21 | 0.12 | 0.20 | 0.11 | 0.24 | 0.13 | 0 | 0 |
| CHDO[20] 1 | 0 | 0.25 | 0.28 | 0.25 | 0.28 | 0.35 | 0.30 | 0 | 0 |
| CHDO 2 | 0 | 0.47 | 0.39 | 0.49 | 0.38 | 0.65 | 0.40 | 0 | 104 |
| DiPDO | 41.9 | 8.84 | 7.45 | 8.75 | 7.51 | 12.4 | 8.65 | 0 | 269 |
| H-HMT1 | 0 | 1.76 | 1.85 | 1.73 | 1.84 | 2.59 | 2.10 | 0 | 417 |
| H-HMT2 | 0 | 0.77 | 0.76 | 0.79 | 0.77 | 1.13 | 0.87 | 17 | 104 |
| 136HT[21] | 378 | 0.35 | 0.34 | 0.31 | 0.31 | 0.57 | 0.32 | 0 | 98 |
| TriPDO | 2.10 | 0.18 | 0 | 0.17 | 0 | 0.30 | 0 | 0 | 0 |
| Quadruple PDO ether | 0.35 | 541 | 0 | 371 | 0 | 895 | 0 | 0 | 0 |

[11]Residual water distillation
[12]Intermediate boiler distillation
[13]Distillation-purification
[14]Methanol
[15]Allyl alcohol
[16]3-ethoxypropanol
[17]3-hydroxymethyl tetrahydropyrane
[18]2-(2-Hydroxymethyl)-1,3-dioxane
[19]2-methyl-1,5-pentanediol
[20]1,4-cyclohexanediol
[21]1,3,6-hexanetriol

Splitting of Diglyme

TABLE 9

Splitting of diglyme.

| Number | T (° C.) | Operating Time Reactor (h) | U (%) | MeOH | Diglyme | Unknown |
|---|---|---|---|---|---|---|
| 1 | 150 | 1.5 | 20.1 | 0.1 | 98.8 | 0 |
| 2 | 220 | 2.25 | 17.8 | 1.1 | 94.5 | 3.6 |
|  |  | 3.25 | 10.3 | 1.2 | 94.1 | 4.0 |
| 3 | 240 | 4.75 | 14.1 | 3.8 | 81.2 | 12.8 |

The conversion does not increase above 20%. Only at a temperature of 240° C. does a somewhat intensified splitting occur.

Splitting of Diglycol

TABLE 10

Splitting of diglycol.

| No. | T (° C.) | Operating time reactor (h) | U (%) | S (EG[22]) (%) | MeOH | 1,4-dioxane | EG | Diglycol |
|---|---|---|---|---|---|---|---|---|
| 1 | 240 | 2 | 7.5 | 37.8 | 0.4 | 2.0 | 2.9 | 93.8 |
| 2 | 280 | 3.75 | 47.9 | 55.7 | 6.9 | 15.9 | 24.9 | 48.4 |
|  |  | 4.75 | 54.4 | 49.9 | 7.4 | 16.1 | 27.0 | 45.3 |

[22]EG: Ethyleneglycol

Diglycol can be split at 280° C. at a conversion from 54% to 50% selectively into ethylene glycol.

Splitting of DiPG

TABLE 11

Splitting of DiPG.

| No. | T (° C.) | Operating time reactor (h) | U (%) | S (1,2-PDO) (%) | Ac | 1,2-PDO | Unknown | DiPG |
|---|---|---|---|---|---|---|---|---|
| 1 | 200 | 1 | 3.7 | 0 | 2.2 | 0 | 4.3 | 82.2 |
|  |  | 2 | 3.9 | 0 | 2.3 | 0 | 4.4 | 82.0 |
| 2 | 220 | 1 | 81.5 | 1.0 | 2.8 | 3.7 | 0 | 80.5 |
| 3 | 250 | 2.5 | 93.4 | 15.7 | 35.1 | 24.1 | 12.8 | 10.8 |
|  |  | 3.5 | 95.4 | 14.5 | 40.5 | 22.3 | 13.4 | 7.4 |
| 4 | 280 | 4.75 | 9.9 | 2.1 | 43.4 | 6.8 | 19.2 | 0.2 |

In the temperature range from 200 to 280° C. the conversion can be increased to almost 100%, but little if any of the desired 1,2-PDO was formed or only with maximally 16% selectivity (250° C.), rather increasingly acrolein.

Splitting of DiPGME

TABLE 12

Splitting of DiPGME.

| No. | T (° C.) | Operating time reactor (h) | U (%) | S (1,2-PDO) (%) | MeOH | Ac | Unknown | 1,2-PDO | DiPGME |
|---|---|---|---|---|---|---|---|---|---|
| 1 | 200 | 1 | 71.4 | 0 | 0 | 1.0 | 0 | 0 | 87.3 |
| 2 | 240 | 1 | 67.4 | 2.9 | 2.2 | 7.9 | 3.7 | 4.0 | 67.8 |

TABLE 12-continued

Splitting of DiPGME.

| No. | T (° C.) | Operating time reactor (h) | U (%) | S (1,2-PDO) (%) | MeOH | Ac | Unknown | 1,2-PDO | DiPGME |
|---|---|---|---|---|---|---|---|---|---|
|  |  | 2 | 62.7 | 13.6 | 5.9 | 16.8 | 6.7 | 8.2 | 35.7 |
| 3 | 260 | 3.75 | 96.5 | 4.9 | 21.6 | 31.0 | 4.9 | 6.0 | 4.4 |
|  |  | 4.75 | 97.0 | 4.9 | 22.0 | 30.9 | 4.8 | 5.9 | 3.7 |

In the range of 200–260° C. the conversion increases up to 97%, although in this case acrolein (31%) and MeOH (22%) were formed more intensively.

Splitting of PGPE

TABLE 13

Splitting of PGPE.

| No. | T (° C.) | Operating time reactor (h) | U (%) | S (PrOH) (%) | Ac | PrOH | PGPE | Unknown |
|---|---|---|---|---|---|---|---|---|
| 1 | 150 | 1 | 54.1 | 0 | 0 | 0 | 94.0 | 4.7 |
|  |  | 2.5 | 43.8 | 0 | 0 | 0 | 93.9 | 4.7 |
| 2 | 180 | 3.5 | 52.5 | 0 | 0 | 0 | 94.3 | 4.7 |
| 3 | 200 | 2.25 | 24.9 | 4.5 | 0 | 1.4 | 91.7 | 4.5 |
|  |  | 3.75 | 24.0 | 4.9 | 0 | 1.4 | 91.7 | 4.5 |
| 4 | 240 | 4.75 | 26.7 | 88.8 | 9.8 | 20.4 | 62.9 | 2.7 |
| 5 | 270 | 1 | 83.7 | 31.9 | 21.6 | 45.3 | 27.6 | 0.9 |
|  |  | 3 | 91.7 | 59.6 | 25.3 | 59.5 | 9.0 | 0.1 |

At 270° C. one achieves both the highest conversion (92%), as well as the highest PrOH selectivity (60%). The main byproduct was Ac with 25%.

Although particular embodiments of the present invention have been described in the foregoing description, it will be understood by those skilled in the art that the invention is capable of numerous modifications, substitutions and rearrangements without departing from the spirit or essential attributes of the invention.

What is claimed is:

1. A process for the production of 1,3-propanediol including the steps:
   a) hydrating acrolein in the presence of an acid hydration catalyst;
   b) catalytically hydrogenating the reaction mixture of step (a), which reaction mixture comprises 3-hydroxypropionaldehyde and is freed of unreacted acrolein;
   c) refining the reaction mixture of step (b) containing water, 1,3-propanediol and by-products boiling higher than 1,3-propanediol, said by-products containing at least one compound selected from the group consisting of 4-oxa-1,7-heptanediol and 4-hydroxy-3-hydroxymethyl tetrahydropyran; and
   d) treating 4-oxa-1,7-heptanediol to form 1,3-propanediol by (1) removing a boiler sump comprising 4-oxa-1,7-heptanediol from the refining step (c), (2) treating the boiler sump in an aqueous solution in the presence of an acid catalyst at about 200 to about 300° C. to form a solution comprising 1,3-propanediol, (3) neutralizing the solution obtained in step (2), and returning the neutralized solution from step (3) to the refining step (c).

2. The process of claim 1 wherein the acid catalyst is a mineral acid.

3. The process of claim 1 wherein the acid catalyst is a mineral acid selected from the group consisting of $H_2SO_4$, $H_3PO_4$ or $HNO_3$, and mixtures thereof.

4. The process of claim 1 wherein the acid catalyst is an organic acid.

5. The process of claim 1 wherein the acid catalyst is a organic acid selected from the group consisting of propionic acid, trifluoracetic acid or pyridine hydrochloride, and mixtures thereof.

6. The process of claim 1 wherein the boiler sump further comprises 4-hydroxy-3-hydroxymethyl tetrahydropyran.

7. The process of claim 1 wherein the acid catalyst is used in an amount of about 0.05 to about 5 weight %, based on the 4-oxa-1,7-heptanediol.

8. The process of claim 1 wherein the acid catalyst is used in an amount of about 0.5 to about 2.5 weight %, based on the 4-oxa-1,7-heptanediol.

9. The process of claim 1 wherein the boiler sump comprises about 50 to about 70 weight % 4-oxa-1,7-heptanediol.

10. The process of claim 1 wherein water is added to the boiler sump to form the aqueous solution.

11. The process of claim 10 wherein the water is added to the sump in an amount so that the ratio of organic compounds in the sump:water is about 0.5:1 to about 1:20.

12. The process of claim 11 wherein the water is added to the sump in an amount so that the ratio of organic compounds in the sump:water is about 1:1 to about 1:8.

13. The process of claim 2 wherein the acid catalyst is used in an amount of about 0.05 to about 5 weight %, based on the 4-oxa-1,7-heptanediol, wherein the boiler sump comprises about 50 to about 70 weight % 4-oxa-1,7-heptanediol, and wherein water is added to the boiler sump to form the aqueous solution in an amount so that the ratio of organic compounds in the sump:water is about 0.5:1 to about 1:20.

14. The process of claim 13 which is a continuous process.

15. The process of claim 13 wherein the acid catalyst is used in an amount of about 0.5 to about 2.5 weight %, based on the 4-oxa-1,7-heptanediol, wherein the water is added to the sump in an amount so that the ratio of organic compound in the sump:water is about 1:1 to about 1:8, and wherein the mineral acid is selected from the group consisting of $H_2SO_4$, $H_3PO_4$ or $HNO_3$, and mixtures thereof.

16. The process of claim 1 having a selectivity of at least 50% and a yield of at least 50%.

17. A process for splitting oligomeric water-soluble ether comprising: (a) treating an aqueous solution comprising oligomeric water-soluble ether in the presence of homogeneous acid catalyst at a temperature of from about 200 to about 300° C. to form the monomer of the oligomeric water-soluble ether; and (b) neutralizing the solution obtained in step (a).

18. The process of claim 17 wherein the aqueous solution further comprises organic compounds having boiling points higher than the oligomeric water-soluble ether.

19. The process of claim 18 wherein the oligomeric water-soluble ether is selected from the group consisting of $C_4$–$C_7$ ethers and mixtures thereof.

20. The process of claim 18 wherein the oligomeric water-soluble ether is selected from the group consisting of 4-oxa-1,7-heptanediol, diethyleneglycol dimethyl ether, diglycol, dipropyleneglycol, dipropyleneglycol methyl ether, and propyleneglycol methyl ether.

21. The process of claim 18 wherein the oligomeric water-soluble ether is 4-oxa-1,7-heptanediol and the monomer is 1,3-propanediol.

22. The process of claim 21 wherein the organic compounds having boiling points higher than the oligomeric water-soluble ether comprise 4-hydroxy-3-hydroxymethyl tetrahydropyran.

23. The process of claim 17 wherein the aqueous solution comprises organic compounds:water in a ratio of about 1:1 to about 1:8.

24. The process of claim 18 wherein the acid is a mineral acid.

25. The process of claim 18 wherein the acid is a mineral acid selected from the group consisting of $H_2SO_4$, $H_3PO_4$ or $HNO_3$, and mixtures thereof.

26. The process of claim 18 wherein the acid is an organic acid.

27. The process of claim 18 wherein the acid is an organic acid selected from the group consisting of propionic acid, trifluoracetic acid or pyridine hydrochloride, and mixtures thereof.

28. The process of claim 18 which is carried out in the absence of a hydrogenation catalyst.

29. The process of claim 18 having a selectivity of at least 50% and a yield of at least 50%.

* * * * *